United States Patent

Aga et al.

[11] Patent Number: 5,922,324
[45] Date of Patent: Jul. 13, 1999

[54] PROPOLIS EXTRACT WITH IMPROVED WATER-SOLUBILITY

[75] Inventors: Hajime Aga; Takashi Shibuya; Shoichi Hamada; Satoshi Iritani; Toshio Miyake, all of Okayama, Japan

[73] Assignee: Kabushiki Kaisha Hayashibara Seibutsu Kagaku Kenkyujo, Okayama, Japan

[21] Appl. No.: 08/827,428

[22] Filed: Mar. 27, 1997

[51] Int. Cl.$^6$ .......................... A61K 35/78; A61K 35/64; A61K 47/00
[52] U.S. Cl. ....................... 424/195.1; 424/439; 424/539; 530/200
[58] Field of Search .................. 424/195.1, 439, 424/539; 530/200

[56] References Cited

U.S. PATENT DOCUMENTS

| | | | |
|---|---|---|---|
| 4,382,886 | 5/1983 | Sosnowski | 530/200 |
| 5,399,349 | 3/1995 | Paunescu et al. | 424/195.1 |
| 5,529,779 | 6/1996 | Hamada et al. | |
| 5,561,116 | 10/1996 | Nakamura et al. | 514/23 |

FOREIGN PATENT DOCUMENTS

| | | |
|---|---|---|
| 0109993 | 6/1984 | European Pat. Off. . |
| 0529962 | 3/1993 | European Pat. Off. . |
| 0622068 | 11/1993 | European Pat. Off. . |
| 2675020 | 10/1992 | France . |
| 5-316968 | 12/1993 | Japan . |
| 6-197734 | 7/1994 | Japan . |
| 6-256177 | 9/1994 | Japan . |
| 6-312918 | 11/1994 | Japan . |
| 8-059491 | 3/1996 | Japan . |
| 8-070797 | 3/1996 | Japan . |
| 8-317762 | 12/1996 | Japan . |
| 95027 | 8/1988 | Romania . |
| 106658 | 6/1993 | Romania . |
| 1169654 | 7/1985 | U.S.S.R. . |
| 2302809 | 2/1997 | United Kingdom . |

OTHER PUBLICATIONS

Dimov, V. et al., "Immunomodulatory action of propolis. Influence on anti–infectious protection and macrophage function.", Apidologie, vol. 22, pp. 155–162 (1991).

Hajime, A. et al., "Isolation and identification of antimicrobial compounds in brazilian proplis.", Bioscience Biotech. Biochem., vol. 58, No. 5, pp. 945–946 (1994).

Donadieu, Y., "Propolis.", Natural Therapeutics, 2nd. Edition (1983).

"Frangrance Journal", No. 83, pp. 20–28, 36–43 (1987)—Translated Portions.

Meresta et al. Bull. Vet. Inst. Pulawy. vol. 24 (1–4), pp. 21–25, 1980.

Japan Abstract 08143462, S. Yoneji et al., vol. 96, No. 10, Jun. 4, 1996.

Japan Abstract 08268885, Zh Oyo Seikagaku Kenkyusho, Oct. 15, 1996.

*Primary Examiner*—Leon B. Lankford, Jr.
*Assistant Examiner*—Christopher R. Tate
*Attorney, Agent, or Firm*—Browdy and Neimark

[57] ABSTRACT

A propolis extract which is prepared by adjusting the pH of propolis to 5.5–7.0 to improve the water-solubility of the effective ingredients of propolis, a composition containing the propolis extract, and a method for improving the water-solubility of propolis extracts.

4 Claims, No Drawings

PROPOLIS EXTRACT WITH IMPROVED WATER-SOLUBILITY

BACKGROUND OF THE INVENTION

1. Field of the Invention

The present invention relates to a propolis extract with an improved water-solubility, more particularly, to a propolis extract wherein the water-solubility of the effective ingredients of propolis is improved by adjusting the pH of the propolis extract to 5.5–7.0, its preparation and uses, and to a method for improving the water-solubility of propolis extracts.

2. Description of the Prior Art

As is described in *Propolis in Natural Therapeutics* (1983), 2nd revised edition, published by Librairie Maloine S. A. Éditeur, Paris, France, *Fragrance Journal*, No. 83, pp. 20–28 and pp. 36–43 (1987), and *Apidologie*, Vol. 22, pp. 155–162 (1991), propolis is a resin-like product, stored by bees in beehives, containing resins, beeswaxes, essential oils, pollens and flavonoids and having been used in a variety of folk medicines for a long time.

It has been known that the main activities of propolis are antiseptic activity, antioxidation activity, anti-inflammatory activity, local anesthesia, virus growth-inhibitory activity, immunoregulatory activity, and macrophage activating activity, and that the main ingredients of propolis are flavonoids, aromatic carboxylic acids, and aromatic aldehydes.

Prior to this invention, the present inventors had studied the effective ingredients of propolis. As a result, they found an effective ingredient, 3-[4-hydroxy-3,5-bis(3-methyl-2-butenyl)phenyl]-2-propenoic acid, alias "Artepillin C" (hereinafter referred to as "substance C" throughout the specification), which exerts an antiseptic activity, hair growth activity, and antitumor activity, and established inventions relating to the uses of substance C: For example, Japanese Patent Laid-Open No. 256,177/94 discloses an antiseptic containing substance C as an effective ingredient, Japanese Patent Laid-Open No. 312,918/94 discloses a hair restorer containing substance C as an effective ingredient, and Japanese Patent Laid-Open No. 191,015/95 discloses an antitumor agent containing substance C as an effective ingredient.

As described above, the present inventors have already shown that substance C is one of the important ingredients in propolis.

Because propolis is a black and brown massive product and because it is mainly composed of water-insoluble hydrophobic products, it could not be readily used and is usually used in the form of a liquid propolis extract or of a propolis tincture by dissolving in and being extracted with high concentration solutions of readily water-soluble organic solvents, for example, acetone, acetic acid, and lower alcohols such as methanol, ethanol, isopropanol (or isopropyl alcohol). In general, ethanol is most favorably used.

Such a propolis extract, however, has a number of drawbacks when used in food products such as heath foods, agents of anti-susceptive diseases such as therapeutic and/or prophylactic agents for susceptive diseases, and cosmetics such as skin-refining agents and skin-whitening agents, and these drawbacks, listed below, render the applicability of propolis to a variety of fields difficult.

(1) The ingredients of the propolis extract such as resins and waxes are readily crystallized. When the propolis extract is diluted with saliva, the ingredients are readily crystallized, and this strongly inhibits their absorption and utilization by living bodies. When the propolis extract is diluted with water, the ingredients are crystallized in quantity, and this renders the handleability very difficult;

(2) The color of the propolis extract is unsatisfactory and the extract easily changes to dark brown or opaque; and (3) The flavor and taste of the propolis extract are unsatisfactory, i.e. it has a muddy smell and a stimulant or sharp taste.

To overcome the drawbacks of conventional propolis extracts, the present inventors continued studying the concentration of readily water-soluble inorganic solvents.

As a result, the inventors established and disclosed in Japanese Patent Laid-Open No. 316,968/93 a purified propolis extract which has an absorbance ratio, $A_{310\ nm}/A_{660\ nm}$, of over 4,000 when the absorbances at 310 nm and 660 nm are converted into those at a concentration of 2 w/w % of the propolis extract, on a dry solid basis (throughout the specification, the wording "on a dry solid basis" is abbreviated as "d.s.b." and the above purified propolis extract may be referred to as "propolis extract), and established a propolis extract obtainable as a fraction by dissolving the effective ingredients of propolis in readily water-soluble inorganic solvents with a concentration of 30–55 v/v %.

During further study of propolis extracts, the present inventors found that when diluted with water according to conventional method, the propolis extracts partly came out of solution and became white suspensions containing insolubilized propolis ingredients. Detailed study revealed that most of the effective ingredients of propolis, especially, substance C, became insoluble.

Further study revealed that the effective ingredients of propolis readily dissolve in water-soluble inorganic solvents with a relatively high or middle concentration, but they are almost insoluble or substantially insoluble in the inorganic solvents when diluted with water, and this results in a serious drawback of hindering the exploitation of the valuable activities of the effective ingredients of propolis.

SUMMARY OF THE INVENTION

The object of the present invention is to produce a propolis extract with an improved water-solubility, biological activity and stability and a satisfactory flavor and taste, as well as to its preparation and uses. To establish such a propolis extract, the present inventors energetically studied propolis extracts.

As a result, the inventors found that the water-solubility of substance C as an effective ingredient of propolis can be greatly improved, and the inherent activities are readily exerted by adjusting the pH of propolis with a normal pH of about 5.0 to a pH of 5.5 or higher, preferably, to a pH of 5.5–7.0, more preferably, to a pH of 5.8–6.4, by the addition of pH-controlling agents, and produced a propolis extract with an improved stability, flavor and taste.

More particularly, the present inventors found that substance C dissolves in dilute aqueous ethanol solutions only in a concentration of 0.03 ppm at 25° C. when a pH-uncontrolled propolis extract, having a normal pH of about 5.0 and containing 10 w/w % propolis extract, d.s.b., in 50 v/v % aqueous ethanol solution, is diluted with water by about 100 folds in accordance with a conventional method, and that the solubility of substance C is improved by at least 15–100 folds in the dilute aqueous ethanol solution by increasing the pH from about 5.0 to 5.5–7.0, and the inherent activity of substance C is readily exerted.

DETAILED DESCRIPTION OF THE INVENTION

The present invention relates to a propolis extract with an improved water-solubility, more particularly, to a propolis extract wherein the water-solubility of the effective ingredients of propolis is improved by adjusting the pH of propolis or extracts thereof to 5.5–7.0, its preparation and uses, and to a method for improving the water-solubility of propolis extracts.

Any method can be used in the present invention as long as the present propolis extract is obtained by adjusting the pH of propolis to 5.5–7.0, preferably, to 5.8–6.4.

In general, the present propolis extract is obtained either by contacting propolis with aqueous solutions of readily water-soluble organic solvents free of pH adjustment to dissolve and extract the effective ingredients of propolis, adjusting the pH of the propolis extract to 5.5–7.0 by pH-controlling agents, and collecting the extract; or by contacting propolis with aqueous solutions of readily water-soluble organic solvents adjusted to a pH of 5.5 or higher, preferably, to a pH of 5.5 or higher but less than 8.0 to dissolve and extract the effective ingredients of propolis, and optionally, adjusting the pH of the propolis extract to 5.5–7.0 by pH-controlling agents before collecting the extract. In this case, the concentration of readily water-soluble organic solvents in the aqueous solutions is generally 70 v/v % or higher. To obtain purified propolis extracts, 30–55 v/v % aqueous solutions of readily water-soluble organic solvents are used in accordance with the method in Japanese Patent Laid-Open No. 316,968/93. Methods to contact propolis with such aqueous solutions and to extract the effective ingredients of propolis are as follows: Dissolving and extracting methods comprising placing propolis in containers, and pouring readily water-soluble organic solvents into the containers. Counter-current extraction methods, comprising cascading columns in series, which had been applied with propolis, and feeding readily water-soluble organic solvents thereunto, can be advantageously used on an industrial-scale production because of their high extraction-efficiency. If necessary, aqueous solutions of 30–55 v/v % readily water-soluble organic solvents containing the effective ingredients of propolis are diluted with water, and the dilutions are contacted with macroporous synthetic adsorbents to adsorb the effective ingredients thereunto, followed by eluting the ingredients from the adsorbents to obtain propolis extracts with an improved water-solubility.

The pH of propolis extracts is adjusted to a pH of 5.5–7.0, preferably, a pH of 5.8–6.4, to obtain high-quality propolis extracts with an improved water-solubility, stability, flavor and taste. When the pH of propolis extracts is lower than 5.5, the water-solubility of substance C is unsatisfactory. When the pH of propolis extracts exceeds 7.0, the extracts contain more colored materials and deteriorate while other effective ingredients such as benzenpropanoic acid 4-(2-carboxyethenyl)-2-(3-methyl-2-butenyl)phenyl ester and flavonoids become unstable. These deteriorate the quality, flavor and taste of the extracts during preservation.

Any pH-controlling agent can be used in the present invention as long as it can control the pH of propolis extracts, particularly, those which can adjust propolis extracts with a concentration of not less than 2 ww %, d.s.b., to the pHs specified in the present invention. For example, alkalies such as magnesium oxide, calcium oxide, sodium hydroxide, potassium hydroxide, magnesium hydroxide, calcium hydroxide, sodium bicarbonate, potassium bicarbonate, sodium carbonate and magnesium carbonate can be used. If necessary, these alkalies can be used in combination with other metal salts such as ferrous hydroxide, zinc carbonate and copper carbonate, and optionally, further used in combination with acids such as hydrochloride, phosphoric acid, acetic acid and citric acid.

Among pH-controlling agents, edible and pharmaceutically-acceptable buffers can be more satisfactorily used in the present invention in an amount of that attains the present object, usually, in an amount of less than 10 w/w % to propolis extracts, d.s.b. After pH-control, propolis extracts can be filtered and centrifuged to obtain fractions containing the effective ingredients of propolis such as substance C, if necessary.

The present propolis extracts thus obtained are 2–25 w/w % propolis solutions, d.s.b., with an improved water-solubility of substance C as an effective ingredient of propolis, and if necessary, the solutions can be arbitrarily concentrated and pulverized into powdery propolis extracts. Furthermore, the propolis concentrates in a liquid form can be arbitrarily dehydrated and pulverized by mixing with anhydrous saccharides such as anhydrous maltose, anhydrous trehalose, and anhydrous lactose, and/or substances such as $\alpha$-, $\beta$- and $\gamma$-cyclodextrins. In the pulverization, the water-solubility of the effective ingredients of propolis contained in the final products can be more improved by using pH-controlling agents such as sodium bicarbonate and magnesium carbonate.

Since the present propolis extract contains the effective ingredients of propolis in a readily absorbable and assimilable form by living bodies, it can be used alone or in combination with one or more other substances such as antioxidants, stabilizers, taste-imparting agents, coloring agents, flavor-imparting agents, filler, adjuvants and excipients. Especially, the activity, effect, stability and handleability of the propolis extract can be satisfactorily improved when used along with one or more vitamins such as tocopherol, carotenoid, L-ascorbic acid, $\alpha$-glycosyl-L-ascorbic acid, rutin and $\alpha$-glycosyl rutin; organic acids such as citric acid and malic acid; and saccharides such as glucose, maltose, trehalose, lactose and maltitol.

Since the present propolis extract exerts the inherent activities of the effective ingredients of propolis, it can be used alone or in combination with one or more other materials in compositions such as food products, cosmetics and agents of anti-susceptive diseases as a supplemental agent for health foods, antiseptics, antioxidants, anti-inflammatories, local anesthetics, virus growth-inhibitory agents, immunoregulatory agents, macrophage activating agents, antitumor agents, hair restorers, antilipemics, ultraviolet-absorbing agents, yellow color-imparting agents, vitamin P-supplementing agents, quality-improving agents or flavor-imparting agents to maintain and promote the health, prevent and/or treat diseases, recover the health from diseases, and maintain and improve skin conditions.

The present propolis extract can be freely used in urine-therapy, which has been known widely and prevailed recently, as a supplemental agent for the urine-therapy to improve the effect and lower the unpleasant smell of urine.

The present propolis extract has a favorable color, flavor and taste so that it well harmonizes with substances having saltiness, astringency, bitterness or taste, and has a strong antiseptic activity. Therefore, the propolis extract can be used not only in specific health foods but also in a variety of compositions such as foods in general including seasonings, Japanese confectioneries, Western cakes, sherbets, ice creams, drinks, spreads, pastes, pickles, processed meats, processed fish meats, milk and egg products, processed vegetables, processed fruits, and processed cereals to improve their flavor, taste, shelf-life and quality stability.

The present propolis extract can be also used in feeds and pet foods for domestic animals, poultry, honey bees, silkworms, and fish as an antiseptic, intestine-controlling agent, vitamin P-supplementing agent, stress-relieving agent, or taste-improving agent.

Furthermore, the present propolis extract can be arbitrarily used in products in the form of a solid, paste or liquid including cosmetics and pharmaceuticals, for example, tobaccos, cigarettes, troches, complex vitamins, sublingual agents, oral refreshing agents, cachous and gargles, nutrients an for intubation feeding, crude drugs, internal medications, injections, dentifrices, lipsticks including those for chapped lips, sunscreens, face-washing soaps, shampoos, rinses, bath salts, agents of anti-susceptive diseases, skin-refining agents, skin-whitening agents, and hair restorers.

The wording "agents of anti-susceptive diseases" as referred to in the present invention means agents for preventing and/or treating susceptive diseases, and the wording "susceptive diseases" as referred to in the present invention means diseases which can be prevented and/or treated by the present propolis extract: Examples of such susceptive diseases are viral diseases, bacterial diseases, traumatic diseases, immunopathies, rheumatisms, diabetes, circulatory diseases, malignant tumors, and nervous diseases.

The present agent of anti-susceptive diseases can be appropriately formed for its final use: For example, it can be formed into agents in the form of a liquid such as a spray, collunarium, nebula, gargle or injection; those in the form of a paste such as an ointment, pap or cream; and those in the form of a solid such as a powder, granule, capsule or tablet.

The dose of the present agent can be controlled depending on the content of propolis extract, administration route or administration frequency. Usually, it is in the range of about 0.0001–10 g/day/adult.

In the case of cosmetics and food products, they can be used similarly as in the case of the above agent of susceptive diseases.

The methods used to incorporate propolis extract into compositions in the present invention include those which can incorporate the propolis extract thereunto: Examples of such methods are mixing, kneading, dissolving, soaking, permeating, spraying, applying, spreading and injecting.

The present invention will be described in detail hereinafter:

EXPERIMENT 1

Confirmation of insolubilized substance C

A propolis mass was disrupted, injected into 3 columns and fed with 50 v/v % aqueous ethanol solution by countercurrent extraction method to dissolve and extract the effective ingredients of propolis. The extract was filtered to obtain a liquid propolis extract containing about 20 w/w % dry solid in a yield of about 30% of the material propolis, d.s.b.

The propolis extract as a sample gave an absorbance ratio, $A_{310\,nm}/A_{660\,nm}$, of 7,365. Throughout the specification, the sample was diluted with 50 v/v % aqueous ethanol solution into a 2 w/w % solution, d.s.b., and measured for absorbance at 660 nm using a 1-cm light-path cell. Similarly the sample was diluted into a 0.004 w/w % solution, d.s.b., and measured for absorbance at 310 nm. The absorbance at 310 nm was multiplied by 500-fold to convert it into that of a 2 w/w % solution, d.s.b., then the ratio of $A_{310nm}/A_{660nm}$ was calculated.

The pH of the sample was 5.0 when measured with a pH-meter. The sample was placed in a beaker and diluted with water by 101-fold into a dilute aqueous ethanol solution in the form of a white suspension which was then allowed to stand at 25° C. for an hour under gentle stirring conditions and centrifuged to obtain a supernatant. High-performance liquid chromatography (HPLC) was used to quantify the concentration of substance C in the supernatant according to the method as described in *Bioscience, Biotechnology, and Biochemistry*, Vol. 58, No. 5, pp. 945–946 (1994). As a control, the sample was diluted by 101-fold with ethanol in place of water. In this case, the sample did not change into a suspension, and the dilution was treated similarly as above to determine the concentration of substance C. Table 1 shows the result.

TABLE 1

|  | Concentration of substance C (ppm) |
|---|---|
| Supernatant of dilution diluted with water | 0.03 |
| Supernatant of dilution diluted with ethanol | 46.7 (Control) |

As is evident from the result in Table 1, it can be seen that the concentration of substance C dissolvable in the supernatant of the dilute aqueous ethanol solution, obtained by diluting a propolis extract with water by 101-fold, was 0.03 ppm. The concentration was only 0.06% of 46.7 ppm of that of the control diluted with ethanol by 101-fold, meaning that most of substance C was insolubilized when diluted with water.

The amount of substance C in the sediments collected by centrifugation was similarly measured by dissolving them in ethanol, revealing that the sediments contained at least 99% substance C in the sample.

The result confirmed that the dilution of a propolis extract with water into a dilute aqueous ethanol solution insolubilized most of substance C.

EXPERIMENT 2

Improvement of water-solubility of substance C

The sample in Experiment 1 was mixed with an equal amount of 50 v/v % aqueous ethanol solution either with or without an adequate amount of sodium hydroxide, and the mixture with a pH 5.0 was adjusted to a pH of 5.2, 5.5, 5.8, 6.0, 6.2, 6.4, 6.8, 7.0, 7.2, 7.5 or 8.1 before prepared into an about 10 w/w % liquid propolis extract, d.s.b., as samples used in the following experiments.

EXPERIMENT 2-(1)

Insolubilization of propolis extract

The influence of pH on the insolubilization of propolis extracts was studied by diluting by 101-fold the samples with different pHs prepared in Experiment 2 into dilute aqueous ethanol solutions in the form of a white suspension, and measuring for turbidity or absorbance at 720 nm using a 1-cm light-path cell.

EXPERIMENT 2-(2)

Water-Solubility of substance C in propolis extract

The influence of pH on the water-solubility of substance C in propolis extracts was studied by diluting the samples with different pHs with water by 101-fold, centrifuging the formed white suspensions similarly as in Experiment 1, and measuring the concentration of substance C in the resulting supernatants.

EXPERIMENT 2-(3)
Coloration degree

The samples with different pHs still remained in the form of a solution even after diluted with ethanol by 21-fold, and the resulting dilutions were measured at 480 nm using a 1-cm light-path cell for studying the influence of pH on the coloration and deterioration of propolis extracts.

EXPERIMENT 2-(4)
Absorbance ratio of $A_{310\,nm}/A_{660\,nm}$

As a condition for stability retaining the quality of propolis extracts, the influence of the pH differences of the samples on the absorbance ratio of $A_{310\,nm}/A_{660\,nm}$ was studied.

EXPERIMENT 2-(5)

After one-month standing at 25° C., the samples were tested similarly as in Experiments 2-(1) to 2-(4) and subjected to a sensory evaluation using 12 panels. The data are shown in Table 2.

tendency was more apparent during preservation, resulting in the deterioration of the samples. It was also revealed that the samples gave a stimulant taste, unpleasant smell and/or deteriorated flavor and taste when preserved at a pH of over 7.

Experiment 2-(4) revealed that the samples should be preserved at a pH of 7.0 or lower to retain their high-quality or to retain a ratio, $A_{310\,nm}/A_{660\,nm}$, of over 4,000 even after a one-month standing.

Summing up the above data, satisfactory propolis extracts, having an improved water-solubility of substance C, as an effective ingredient of propolis, and a satisfactory stability, flavor and taste, are readily produced by adjusting the pH of the propolis extracts to 5.5–7.0, more preferably, to 5.8–6.4 by the addition of pH-controlling agents.

EXPERIMENT 3
Acute toxicity test

Using 7-week-old dd-strain mice, a lyophilized product of a liquid propolis extract with pH 6.4, obtained by the method in Example A-1, was orally administered to the mice for

TABLE 2

| | When prepared | | | | | | After 1-month standing | | | | | | |
|---|---|---|---|---|---|---|---|---|---|---|---|---|---|
| Test No. | X | A | B | C | D | E | A | B | C | D | E | Flavor & Taste** | Total Judgement |
| 1 | 5.0* | 0.224 | 0.03 | 1 | 0.197 | 7,365 | 0.230 | 0.03 | 1 | 0.210 | 6,918 | Satisfactory | No good Control |
| 2 | 5.2 | 0.202 | 0.06 | 2 | 0.197 | 7,187 | 0.205 | 0.07 | 2 | 0.213 | 6,729 | Satisfactory | No good Control |
| 3 | 5.5 | 0.188 | 0.45 | 15 | 0.198 | 6,514 | 0.188 | 0.45 | 15 | 0.215 | 6,375 | Satisfactory | Good Present Invention |
| 4 | 5.8 | 0.176 | 2.30 | 77 | 0.204 | 6,434 | 0.180 | 2.38 | 79 | 0.224 | 6,213 | Satisfactory | Excellent Present Invention |
| 5 | 6.0 | 0.144 | 4.28 | 143 | 0.210 | 6,378 | 0.148 | 4.37 | 146 | 0.231 | 6,023 | Satisfactory | Excellent Present invention |
| 6 | 6.2 | 0.134 | 8.40 | 280 | 0.221 | 6,015 | 0.136 | 8.48 | 283 | 0.245 | 5,682 | Satisfactory | Excellent Present Invention |
| 7 | 6.4 | 0.101 | 13.6 | 453 | 0.248 | 5,659 | 0.102 | 13.8 | 460 | 0.266 | 5,054 | Satisfactory | Excellent Present Invention |
| 8 | 6.8 | 0.078 | 18.7 | 623 | 0.260 | 5,401 | 0.078 | 18.9 | 630 | 0.282 | 4,868 | Almost satisfactory | Good Present Invention |
| 9 | 7.0 | 0.058 | 24.1 | 803 | 0.283 | 4,973 | 0.059 | 24.2 | 807 | 0.305 | 4,054 | Almost satisfactory | Good Present Invention |
| 10 | 7.2 | 0.051 | 28.3 | 943 | 0.303 | 4,614 | 0.053 | 28.3 | 943 | 0.399 | 3,860 | Slightly stimulative, bad smell | No good Control |
| 11 | 7.5 | 0.049 | 31.4 | 1,047 | 0.329 | 4,303 | 0.050 | 31.0 | 1,033 | 0.458 | 3,675 | Stimulative, bad smell | No good Control |
| 12 | 8.1 | 0.041 | 36.4 | 1,213 | 0.464 | 2,935 | 0.044 | 36.2 | 1,207 | 0.588 | 2,320 | Stimulative, bad smell | No good Control |

In Table 2, the symbols "X", "A", "B", "C", "D" and "E" mean as follows:
X, pH of propolis extract;
A, turbidity at 720 nm ($A_{720nm}$);
B, concentration (ppm) of substance C in supernatant;
C, concentration ratio of substance C in supernatant with respect to that of test No. 1, i.e. a dilute aqueous ethanol solution free of pH adjustment;
D, coloration degree at 480 nm ($A_{460nm}$); and
E, absorbance ratio of $A_{310nm}/A_{660nm}$.
The symbols "*" and "**" mean "free of pH control" and "summary of evaluations of 10 or more panels among 12 panels", respectively.

As is evident from the results shown in Table 2, it was revealed that the pH increment of propolis extracts (pH 5.0) from 5.0 to 5.5–7.0, more preferably, to 5.8–6.4 enabled the production of high-quality propolis extracts with an improved water-solubility of substance C and a satisfactory stability, flavor and taste.

Experiment 2-(1) revealed that the turbidity and water-solubility of the samples were respectively lowered and improved as the increase of their pHs, particularly, the properties were lowered and improved up to a pH of about 7.0, and that the turbidity almost did not decrease at a pH of over about 7.0, i.e. there substanially no improvement of water-solubility. Experiment 2-(2) revealed that the water-solubility of substance C, one of the effective ingredients of propolis, was greatly increased when adjusted to a pH of over 5.5. Experiment 2-(3) revealed that the samples were more highly colored, particularly at a pH of over 7, and this acute toxicity test. As a result, no mouse died up to a dose of 2.5 g/kg mouse. This indicates that the product has an extremely-low toxicity. A similar test was conducted using a lyophilized product of a liquid propolis extract with pH 6.2 obtained by the method in Example A-4, and this gave a similar result, meaning that the product was also extremely-low in toxicity.

The following Examples A and B illustrate the present propolis extract with an improved water-solubility and compositions containing the same as an effective ingredient:

EXAMPLE A-1

Propolis was soaked in and extracted with 95 v/v % aqueous ethanol solution in a conventional manner to obtain an extract, and the sediment was washed with a small amount of water to extract the sediment. These extracts were pooled into a crude propolis extract, containing about 20 w/w % dry solids in 80 v/v % aqueous ethanol solution, which was then mixed with water to lower the ethanol concentration to 50 v/v %. The dilution was allowed to stand at 50° C. for an hour to separate into two layers. One layer was an upper layer having the effective ingredients of propolis and the other was a lower layer having sticky sediments. These layers were allowed to stand at ambient temperature overnight, and the upper layer was collected and mixed with sodium bicarbonate to adjust the pH to 6.4, followed by recovering a liquid propolis extract with an absorbance ratio, $A_{310\ nm}/A_{660\ nm}$, of 8,425 and an improved water-solubility in a yield of about 45% of the crude propolis extract, d.s.b.

The product, containing substance C with an improved water-solubility and a satisfactory stability, flavor and taste, can be arbitrarily used alone or in combination with other material(s) in food products, agents of anti-susceptive diseases, and cosmetics as a supplemental health food, antiseptic, antioxidant, immunoregulatory agent, macrophage activating factor, antitumor agent or hair restorer.

EXAMPLE A-2

A propolis mass was disrupted and injected into two columns which were then fed with 50 v/v % aqueous ethanol solution to dissolve and extract the effective ingredients of propolis by counter-current extraction method. The resulting extract was filtered and mixed with sodium carbonate to adjust the pH to 6.2. Thus, a liquid propolis extract with an absorbance ratio, $A_{310\ nm}/A_{660\ nm}$, of 6,015 and an improved water-solubility was obtained in a yield of about 32% to the material propolis, d.s.b.

Similarly as the product in Example A-1, the product contains substance C with an improved water-solubility and has a satisfactory stability, flavor and taste. Therefore, the product can be arbitrarily used alone or in combination with other material(s) in food products, agents of anti-susceptive diseases, and cosmetics as a supplemental health food, antiseptic, antioxidant, immunoregulatory agent, macrophage activating factor, antitumor agent or hair restorer.

EXAMPLE A-3

A propolis mass was disrupted and injected into three columns which were then fed with 50 v/v % aqueous ethanol solution, which had been previously adjusted to pH 7.8 with sodium carbonate, to dissolve and extract the effective ingredients of propolis by counter-current extraction method. The extract was adjusted to pH 6.0 with a pH-controlling agent and filtered to obtain a liquid propolis extract with an absorbance ratio, $A_{310\ nm}/A_{660\ nm}$, of 6,438 and an improved-water solubility. The yield was about 30% to the material propolis, d.s.b.

Similarly as the product in Example A-1, the product contains substance C with an improved water-solubility and has a satisfactory stability, flavor and taste. Therefore, the product can be arbitrarily used alone or in combination with other material(s) in food products, agents of anti-susceptive diseases, and cosmetics as a supplemental health food, antiseptic, antioxidant, immunoregulatory agent, macrophage activating factor, antitumor agent or hair restorer.

EXAMPLE A-4

An 80 v/v % aqueous ethanol solution, containing a crude propolis extract obtained by the method in Example A-1, was lowered its ethanol concentration to 45 v/v % according to the method in Example A-1 to separate into two layers, i.e. upper and lower layers, which were then allowed to stand at ambient temperature for 5 hours. The upper layer was collected and diluted with an equal amount of water, and the dilution was fed to a column packed with "AMBERLITE XAD-7", a synthetic macroporous resin commercialized by Rohm & Haas Co., Philadelphia, Pa., USA, washed with water, and fed with 95 v/v % aqueous ethanol solution to elute the effective ingredients of propolis. The resulting eluate was mixed with sodium bicarbonate to adjust the pH to 6.2 to obtain a liquid propolis extract with an absorbance ratio, $A_{310\ nm}/A_{660\ nm}$, of 21,892 and an improved water-solubility. The yield was about 22% of the crude propolis extract, d.s.b.

Similarly as the product in Example A-1, the product contains substance C with an improved water-solubility and has a satisfactory stability, flavor and taste. Therefore, the product can be arbitrarily used alone or in combination with other material(s) in food products, agents of anti-susceptive diseases, and cosmetics as a supplemental health food, antiseptic, antioxidant, immunoregulatory agent, macrophage activating factor, antitumor agent or hair restorer.

EXAMPLE B-1

Gummy candy

One hundred parts by weight of "MABIT®", a hydrogenated maltose syrup commercialized by Hayashibara Shoji, Inc., Okayama, Japan, and 50 parts by weight of "TREHAOSE™", a high-purity hydrous crystalline trehalose commercialized by Hayashibara Shoji, Inc., Okayama, Japan, were heated and concentrated under a reduced pressure into a concentrate with a moisture content of about 15 w/w %. The concentrate was in a conventional manner mixed with 13 parts by weight of gelatin dissolved in 18 parts by weight of water, one part by weight of a liquid propolis extract obtained by the method in Example A-1, 2 parts by weight of sodium citrate, and adequate amounts of a coloring agent and a flavor. The mixture thus obtained was shaped and packed into a desired product.

The product is a gummy candy with a satisfactory texture and flavor and free of dental-caries inducibility.

EXAMPLE B-2

Chewing gum

Three parts by weight of a gum base was melted by heating until it softened, and the resultant was mixed with 4 parts by weight of sucrose and 3 parts by weight of "TREHAOSE™", 0.02 part by weight of a liquid propolis extract obtained by the method in Example A-1, and an adequate amount of a coloring agent, and the mixture was kneaded by a roll, shaped and packed to obtain a desired product.

The product is a chewing gum which has a satisfactory texture, flavor and taste and induces fewer dental caries because it contains the effective ingredients of propolis.

EXAMPLE B-3

Gyuhi (starch paste)

One part by weight of glutinous rice starch was mixed with 1.2 parts by weight of water, and the mixture was gelatinized by heating and further mixed with 1.5 parts by weight of "TREHAOSE™", 0.7 part by weight of "SUNMALT®", a hydrous crystalline maltose commercialized by Hayashibara Co., Ltd., Okayama, Japan, 0.3 part by weight of starch hydrogenate, and 0.02 part by weight of a liquid propolis extract obtained by the method in Example A-2. The mixture thus obtained was in a conventional manner shaped and packed to obtain a desired product.

The product is a Japanese confectionery which has a natural flavor and taste, as well as a satisfactory biting property, a relatively-long shelf life and stability because of the effective ingredients of propolis.

EXAMPLE B-4

Cream filling

One thousand parts by weight of "FINETOSE®", an anhydrous crystalline maltose commercialized by Hayashibara Co., Ltd., Okayama, Japan, 200 parts by weight of anhydrous crystalline trehalose, 1,000 parts by weight of shortening, 50 parts by weight of a cacao mass, 3 parts by weight of a liquid propolis extract obtained by the method in Example A-3, and one part by weight of lecithin were mixed in a conventional manner to obtain a cream filling.

The product, having a satisfactory stability and shelf-life due to the effective ingredients of propolis, has a pleasant biting property and meltability in the mouth.

EXAMPLE B-5

Butter cake

Fifty parts by weight of unsalted butter, 50 parts by weight of shortening, 50 parts by weight of honey, and 130 parts by weight of sugar were well mixed, and further mixed and stirred with 150 parts by weight of eggs. The resulting mixture was mixed with 135 parts by weight of wheat flour, 75 parts by weight of milk, 4 parts by weight of sodium bicarbonate, and an adequate amount of vanilla flavor. The mixture thus obtained was in a conventional manner poured into a mold, baked up and cooled to ambient temperature. A syrup, obtained by mixing 1.5 parts by weight of a liquid propolis extract obtained by the method in Example A-1, 20 parts by weight of a Japanese apricot liqueur, and 20 parts by weight of a cognac, was painted with a brush onto the surface of the above baked product to obtain a desired product.

The product, having a satisfactory flavor and taste and containing the effective ingredients of propolis, can be arbitrarily used to maintain and/or promote health and prevent and/or treat diseases, as well as to promote the recovery of health from diseases.

EXAMPLE B-6

Ice cream

Two thousand and three-hundred parts by weight of milk was heated to about 60° C. and mixed at that temperature with 200 parts by weight of egg yolks, 50 parts by weight of eggs, 420 parts by weight fructose, 30 parts by weight of starch hydrogenate, 200 parts by weight of fresh cream, 20 parts by weight of evaporated milk, 3 parts by weight of a liquid propolis extract obtained by the method in Example A-2, and one part by weight of a gelatin powder. The mixture was sterilized by heating at 75° C. for 15 minutes, cooled, mixed with 20 parts by weight of a Japanese apricot liqueur under stirring conditions, poured into a container and frozen to obtain a desired product.

The product containing the effective ingredients of propolis can be arbitrarily used to maintain and/or promote the health and prevent and/or treat diseases, as well as to promote the recovery of health from diseases.

EXAMPLE B-7

Powdery Propolis Extract

Five parts by weight of a liquid propolis extract obtained by the method in Example A-2 was mixed with 7 parts by weight of anhydrous crystalline maltose, and the mixture was dried by air heated to 40° C. for an hour, and further mixed to homogeneity with 3 parts by weight of anhydrous crystalline trehalose and 0.05 part by weight of sodium bicarbonate to obtain a powdery propolis extract. One g aliquots of the powder were distributed to laminated aluminum containers.

Since the product readily disperses and dissolves in water and has a satisfactory taste preference, it can be arbitrarily used alone as a health food, antiseptic, medicine, flavor-imparting agent, deodorant or agent for urine-therapy, and used as a material for other compositions. The product can be also used to maintain and/or promote health and prevent and/or treat diseases, as well as to promote the recovery of health from diseases.

When used as a health food, the product can be used alone or used after dispersing and dissolving in liquids such as teas, milk or juice in an amount of 0.2–1 g per 200 ml of the liquid. The product can be also used in urine-therapy by dissolving in fresh urine in an amount of 0.5–2 g per 100 ml urine.

EXAMPLE B-8

Powdery propolis extract

To 5 parts by weight of a liquid propolis extract obtained by the method in Example A-4 were added 2 parts by weight of γ-cyclodextrin and 5 parts by weight of anhydrous crystalline trehalose. The mixture was dried by air heated to 40° C. for an hour, then mixed to homogeneity with 7 parts by weight of anhydrous crystalline maltose powder to obtain a powdery propolis extract. One g aliquots of the powder were distributed to laminated aluminum containers.

Similarly as the product of Example B-7, the product readily disperses and dissolves in water and has a pleasant taste. Therefore, the product can be used alone as a health food, antiseptic, medicine, flavor-imparting agent, deodorant or agent for the urine-therapy, and used as a material for other compositions. The product can be also used to maintain and/or promote health and prevent and/or treat diseases, as well as to promote the recovery of health from diseases.

EXAMPLE B-9

Formula feed

A formula feed was prepared by mixing 30 parts by weight of wheat bran flour, 30 parts by weight of a powdery propolis extract obtained by the method in Example B-7, 10 parts by weight of skim milk, 10 parts by weight of a powder containing lactosucrose, 10 parts by weight of complex vitamins, 5 parts by weight of fish flour, 5 parts by weight of calcium secondary phosphate, 3 parts by weight of liquid oil and fat, 3 parts by weight of calcium carbonate, 2 parts by weight of salt, and 2 parts by weight of minerals.

The product exerts a satisfactory growth-promoting activity for bifid bacteria in addition to the activities of the effective ingredients of propolis, and it can be arbitrarily used to prevent infectious diseases and diarrhea of domestic animals, promote their appetite and growth, and prevent unsatisfactory smell of their feces. If necessary, the product can be used in combination with other feed material(s), for example, concentrates such as cereals, wheat flours, starches, oil meals, and lees or meals, and materials for roughages such as rice straws, hays, bagasses, corncobs and their silages.

EXAMPLE B-10

Tablet

Thirty parts by weight of a powdery propolis extract obtained by the method in Example B-7, 20 parts by weight of "NYUKAOLIGO® LS-55P)", a powder containing lactosucrose commercialized by Hayashibara Shoji, Inc., Okayama, Japan, 10 parts by weight of calcium lactate, 5 parts by weight of L-ascorbic acid, 5 parts by weight of pullulan, one part by weight of α-glycosyl rutin, 0.2 part by weight of magnesium carbonate, one part by weight of calcium tertiary phosphate, one part by weight of sugar ester, and an adequate amount of a powdery flavor were mixed to homogeneity. The mixture was tabletted by a tabletting machine, having a 20R punch and a diameter of 12 mm, to obtain a tablet. Using a sugar coating machine, the tablet was coated in a conventional manner with an aqueous solution heated to 55° C. containing 50 w/w % "TREHAOSE™" and 0.2 w/w % pullulan and dried. The coating step was repeated to obtain a sugar coated tablet with a plain surface containing a crystallized hydrous crystalline trehalose.

Usually, the product, which is free of cracking and has a satisfactory stability and swallowability, is orally administered to humans at a dose of about 1–40 tablets/day/adult, preferably, a dose of about 2–20 tablets/day/adult. Since the product has the activities of effective ingredients of propolis and is enriched with lactosucrose and pullulan, it exerts a strong intestine-controlling activity. Thus, the product is satisfactorily used as an orally administrable product to prevent colon cancers. Because the product is enriched with calcium salts, it can be advantageously used as an orally administrable product to prevent and/or treat osteoporosis, and because the product is enriched with L-ascorbic acid and α-glycosyl rutin, it can be satisfactorily used as an orally administrable product to promote health and prevent senescence.

EXAMPLE B-11

Tablet

Ten parts by weight of a powdery propolis extract obtained by the method in Example B-8, 70 parts by weight of trehalose, 62 parts by weight of corn starch, and 8 parts by weight of fatty acid sucrose ester were mixed to homogeneity and tabletted similarly as in Example B-10 to obtain a tablet. To prepare into a tablet readily dissolvable in the stomach, the above product is sugarcoated after being pre-coated with 5 w/w % hydroxypropylmethylcellulose, while the above product is coated with 10 w/w % hydroxypropylmethylcellulose to prepare an enteric-coated tablet.

These tablets can be advantageously used as an agent to treat human malignant tumors such as stomach cancer, lung cancer, hepatoma, hysterocarcinoma, breast cancer, colon cancer and melanoma.

EXAMPLE B-12

External medicine

To 300 parts by weight of a maltose powder and 200 parts by weight of trehalose were added 20 parts by weight of an upper layer, containing the effective ingredients of propolis obtained by the method in Example A-4 and 33 parts by weight of methanol, and further added 200 parts by weight of 10 w/w % aqueous pullulan solution to obtain an ointment for traumatic injuries with an appropriate extendibility and adhesiveness.

The product exerts satisfactory antiseptic, anti-inflammatory, antitumor and local anesthetic activities due to the effective ingredients of propolis and exerts an activity of supplementing energy to living cells due to the presence of maltose and trehalose. Because of these activities, the product shortens the healing period and satisfactorily cures the injured skin tissues.

EXAMPLE B-13

Injection

A liquid propolis extract obtained by the method in Example A-4 was dissolved in 30 v/v % aqueous ethanol solution, and the resulting solution was membrane filtered in a conventional manner to obtain a pyrogen-free solution which was then distributed to 20-ml ampoules to give 5 mg/ampoules of the propolis extract, d.s.b., lyophilized and sealed to obtain a desired product.

The product can be used alone or in combination with other vitamin(s) and/or mineral(s) before being administered intramuscularly or intravenously to humans. The product can be arbitrarily used to promote the treatment of diseases such as immunopathies, circulatory diseases, nervous diseases and malignant tumors, and used to recover health from such diseases.

EXAMPLE B-14

Injection

Six parts by weight of sodium chloride, 0.3 part by weight of potassium chloride, 0.2 part by weight of calcium chloride, 3.1 parts by weight of sodium lactate, 45 parts by weight of trehalose, and 0.1 part by weight of a liquid propolis extract obtained by the method in Example A-4 were dissolved in 1,000 parts by weight of 2 v/v % aqueous ethanol solution. The resulting solution was membrane filtered in a conventional manner to obtain a pyrogen-free solution, and 25-ml aliquots were distributed to plastic containers to obtain a desired product.

The product can be used as a vitamin P-, energy- or mineral-supplementing agent to promote the treatment of diseases and promote the recovery of health from diseases.

EXAMPLE B-15

Agent for intubation feeding

A composition was prepared by mixing 20 parts by weight of anhydrous trehalose, 1.1 parts by weight of glycine, 0.18 part by weight of sodium glutamate, 1.2 parts by weight of salt, one part by weight of sodium citrate, 0.4 part by weight of calcium lactate, 0.1 part by weight of magnesium carbonate, 0.1 part by weight of a powdery propolis extract obtained by the method in Example B-7, 0.01 part by weight of thiamine, and 0.01 part by weight of riboflavin. Twenty-four g aliquots of the composition were distributed to laminated aluminum small bags, and the bags were heat-sealed to obtain an agent for intubation feeding.

The product can be used as an energy-supplementing solution administrable orally or parenterally to the nasal cavity, stomach or intestines by intubation feeding after dissolving one bag of the product in about 300–500 ml water.

EXAMPLE B-16

Bath salts

Twenty-one parts by weight of DL-sodium lactate, 8 parts by weight of sodium pyruvate, 3 parts by weight of trehalose, 5 parts weight of a liquid propolis extract obtained by the method in Example A-3, and 37 parts by weight of ethanol were mixed with 26 parts by weight of refined water, and adequate amounts of a coloring agent and a flavor to obtain a bath salts.

The product can be used as a skin-refining agent or skin whitening-agent by it dissolving in a bath tab with hot water to dilute it by 100–10,000 folds. Similarly as above, the a product can be used after diluting it in a cleansing liquid or lotion.

EXAMPLE B-17

Milky lotion

A half part by weight of polyoxyethylene behenyl ether, one part by weight of polyoxyethylene sorbitol tetraoleate, one part by weight of oil-soluble glyceryl monostearate, 0.5 part by weight of pyruvic acid, 0.5 part by weight of behenyl alcohol, one part by weight of avocado oil, one part by weight of a liquid propolis extract obtained by the method in Example A-2, and adequate amounts of vitamin E and an antiseptic were dissolved by heating in a conventional manner. The mixture was admixed with 0.5 part by weight of L-sodium lactate, 0.5 part by weight of trehalose, 5 parts by weight of 1,3-butylene glycol, 0.1 part by weight of carboxy vinylpolymer, and 84.3 parts by weight of refined water, and emulsified by a homogenizer. The emulsion was mixed with an adequate amount of a flavor to obtain a milky lotion.

The product can be used as a sunscreen, skin-refining agent or skin-whitening agent.

EXAMPLE B-18

Cream

Two parts by weight of polyoxyethylene glycol monostearate, 5 parts by weight of self-emulsifying glycerine monostearate, 2 parts by weight of a liquid propolis extract obtained by the method in Example A-3, one part by weight of liquid paraffin, 10 parts by weight of glyceryl trioctanate, and an adequate amount of an antiseptic were mixed. The mixture was dissolved by heating, then mixed with 2 parts by weight of trehalose, 5 parts by weight of 1,3-butylene glycol, and 66 parts by weight of refined water, followed by emulsifying the mixture with a homogenizer and admixing with an adequate amount of a flavor to obtain a cream.

The product can be used as a sunscreen, skin-refining agent or skin-whitening agent.

EXAMPLE B-19

Shampoo

A shampoo was prepared by dissolving by heating 1.0 part by weight of a liquid propolis extract obtained by the method in Example A-4, 0.2 part by weight of alkyldiaminoethylglycine hydrochloride solution, 20.0 parts by weight of lauryl dimethylaminoacetic acid betaine, 25.0 parts by weight of lauroylmethyl tauride, and 52.0 parts by weight of refined water, adequate amounts of an antiseptic and a flavor.

Since the product has a satisfactory hair-washing ability and causes less damage to hair, it can be arbitrarily used to promote the growth of hair or fur of animals including humans and treat and/or prevent dandruff, itchy scalp, and falling hair.

EXAMPLE B-20

Rinse

Two and half parts by weight of a liquid propolis extract obtained by the method in Example A-1, 2.0 parts by weight of distearyldimethylammonium chloride, 2.0 parts by weight of cetanol, 2.0 parts by weight of silicone oil, 1.0 part by weight of polyoxyethylene oleylalcoholether, and an adequate amount of a flavor were dissolved by heating. The mixture was mixed under stirring conditions with a mixture consisting of 3.0 parts by weight of 1,3-butylene glycol, 89.0 parts by weight of refined water, and an adequate amount of an antiseptic, and the resulting mixture was cooled and allowed to stand to obtain a rinse.

The product effectively rinses hair and can be arbitrarily used to promote the growth of hair or fur of animals including humans and treat and/or prevent dandruff, itch of scalp, and falling hair.

EXAMPLE B-21

Hair tonic

Two parts by weight of "αG RUTIN", an α-glycosyl rutin commercialized by Toyo Sugar Refining Co., Ltd., Tokyo, Japan, and 20.0 parts by weight of glycerine were mixed with and dissolved in 550 parts by weight of refined water heated to 60° C., and the mixture was mixed with a solution, prepared by dissolving in 440 parts by weight of ethanol 0.05 part by weight of "KANKOSO 301 (6-[2-[(5-bromo-2-pyridyl)amino]vinyl]-1-ethyl-2-picolinium iodide)", a cyanine dye commercialized by Photosensitizing Dyes Co., Ltd., Okayama, Japan, and 10 parts by weight of a liquid propolis extract obtained by the method in Example A-2, and a solution prepared by dissolving 2.0 parts by weight of l-menthol in 10 parts by weight of ethanol. The resulting mixture was filtered and bottled to obtain a hair tonic.

The product effectively promotes the growth of hair and treat and/or prevent alopecia and hair loss, and it can be satisfactorily used to prevent dandruff and itchy scalp and used as a remedy for traumatic injuries because it has satisfactory antiseptic and antiphlogistic activities.

EXAMPLE B-22

Hair liquid

A composition was prepared by mixing 55.0 parts by weight of ethanol, 20.0 parts by weight of polyoxypropylene (40) butylether, and 13.0 parts by weight of refined water with 1.0 part by weight of a liquid propolis extract obtained by the method in Example A-1, and 3.0 parts by weight of 2-O-α-D-glucopyranosyl-L-ascorbic acid. The composition was mixed in a conventional manner with adequate amounts of a pH-controlling agent, flavor and antiseptic to obtain a hair liquid.

The product effectively promotes the growth of hair and treats and/or prevents alopecia and hair loss, and it can be satisfactorily used to prevent dandruff and itch of scalp and used as a remedy for traumatic injuries because it has satisfactory antiseptic and antiphlogistic activities.

EXAMPLE B-23

Hair cream

A composition was prepared by mixing 3.0 parts by weight of beeswax, 15.0 parts by weight of petrolatum, 42.0 parts by weight of liquid paraffin, 3.0 parts by weight of polyoxyethylene (5) stearate, 2.0 parts by weight of polyoxyethylene (6) oleylalcoholether, 1.0 part by weight of polyoxyethylene (6) cetylalcoholether, 1.0 part by weight of a liquid propolis extract obtained by the method in Example A-3, 0.3 part by weight of 2-O-α-D-glucopyranosyl-L-ascorbic acid, and 32 parts by weight of refined water. The composition was mixed in a conventional manner with adequate amounts of a pH-controlling agent, flavor and antiseptic to obtain a hair cream.

The product can be used to promote the growth of hair and treat and/or prevent alopecia and hair loss, as well as dandruff and itchy scalp.

EXAMPLE B-24

Toothpaste

A toothpaste consisting of the ingredients below was prepared. The product with an antiseptic activity can be satisfactorily used to prevent foul breath and dental caries.

| Composition | |
| --- | --- |
| Calcium phosphate, dibasic | 45.0 parts by weight |
| Pullulan | 2.95 parts by weight |
| Sodium lauryl sulfate | 1.5 parts by weight |
| Glycerine | 20.0 parts by weight |
| Polyoxyethylene sorbitan laurate | 0.5 part by weight |
| Antiseptic | 0.05 part by weight |
| Liquid propolis extract obtained | 12.0 parts by weight |

-continued

| Composition | |
|---|---|
| by the method in Example A-3 | |
| Maltitol | 5.0 parts by weight |
| Water | 13.0 parts by weight |

As is described in the above, the present invention relates to a propolis extract with an improved water-solubility of the effective ingredients of propolis, especially, substance C, and provides a propolis extract which readily exerts the activities of the effective ingredients of propolis and has a satisfactory stability, flavor and taste.

The present propolis extract is not restricted to be used in conventional high-concentration solutions of highly stimulative and readily water-soluble organic solvents, and it can be freely used in lower concentration solutions of such organic solvents. Thus, the present propolis extract can be arbitrarily used in compositions such as food products, agents of anti-susceptive diseases, and cosmetics.

The present propolis extract, having an absorbance ratio, $A_{310\ nm}/A_{660\ nm}$, of over 4,000, and a satisfactory color, flavor and taste, would give an unfathomable influence on the fields of food products, cosmetics and pharmaceuticals.

While there has been described what is at present considered to be the preferred embodiments of the invention, it will be understood the various modifications may be made therein, and it is intended to cover in the appended claims all such modifications as fall within the true spirits and scope of the invention.

We claim:

1. A method for preparing a propolis extract solution having a pH of 5.5–7.0 to improve the water solubility of the effective ingredients of propolis comprising:

contacting a propolis mass with an aqueous solution of a readily water soluble organic solvent free of pH adjustment to dissolve and extract the effective ingredients of said propolis mass;

adjusting the pH of the resulting propolis extract solution to 5.5–7.0 by the addition of a pH-controlling agent; and collecting the propolis extract solution, wherein the collected propolis extract solution has a pH of 5.5–7.0 and contains 3-[4-hydroxy-3,5-bis (3-methyl-2-butenyl) phenyl]-2-propenoic acid as an active ingredient, and whereby said active ingredient dissolves in an aqueous ethanol solution of 0.5 v/v% ethanol in an amount of at least 0.45 ppm of active ingredient at 25° C.

2. A method for preparing a propolis extract solution having a pH of 5.5–7.0 to improve the water solubility of the effective ingredients of propolis comprising:

contacting a propolis mass with an aqueous solution of a readily water soluble organic solvent adjusted to a pH of 5.5 or higher by the addition of a pH-controlling agent to dissolve and extract the effective ingredients of said propolis mass;

optionally adjusting the pH of the resulting propolis extract solution; and collecting the propolis extract solution, wherein the collected propolis extract solution has a pH of 5.5–7.0 and contains 3-[4-hydroxy-3,5-bis (3-methyl-2-butenyl) phenyl]-2-propenoic acid as an active ingredient, and whereby said active ingredient dissolves in an aqueous ethanol solution of 0.5 v/v% ethanol in an amount of at least 0.45 ppm of active ingredient at 25° C.

3. A propolis extract solution which has a pH of 5.5–7.0 and contains 3-[4-hydroxy-3,5-bis (3-methyl-2-butenyl) phenyl]-2-propenoic acid as an active ingredient, whereby said active ingredient dissolves in an aqueous ethanol solution of 0.5 v/v% ethanol in an amount of at least 0.45 ppm of active ingredient at 25° C., which is prepared by the method of claim 1.

4. A propolis extract solution which has a pH of 5.5–7.0 and contains 3-[4-hydroxy-3,5-bis (3-methyl-2-butenyl) phenyl]-2-propenoic acid as an active ingredient, whereby said active ingredient dissolves in an aqueous ethanol solution of 0.5 v/v% ethanol in an amount of at least 0.45 ppm of active ingredient at 25° C., which is prepared by the method of claim 2.

* * * * *